United States Patent
Otsubo et al.

(10) Patent No.: US 7,060,058 B2
(45) Date of Patent: Jun. 13, 2006

(54) DISPOSABLE PANTS-TYPE DIAPER HAVING FRONT PANEL WITH ELASTICIZED LOWER EDGE

(75) Inventors: Toshifumi Otsubo, Kagawa-ken (JP); Hiroki Yamamoto, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 466 days.

(21) Appl. No.: 10/120,174

(22) Filed: Apr. 11, 2002

(65) Prior Publication Data

US 2002/0151864 A1 Oct. 17, 2002

(30) Foreign Application Priority Data

Apr. 12, 2001 (JP) ............... 2001-114563

(51) Int. Cl.
- *A61F 13/475* (2006.01)
- *A61F 13/49* (2006.01)
- *A61F 13/196* (2006.01)
- *A61F 13/72* (2006.01)

(52) U.S. Cl. .................. 604/385.27; 604/385.26; 604/385.25; 604/385.24; 604/385.23; 604/385.3; 604/396; 604/386

(58) Field of Classification Search ........ 604/358–402; D24/126
See application file for complete search history.

(56) References Cited

U.S. PATENT DOCUMENTS

| | | | |
|---|---|---|---|
| 4,743,241 A * | 5/1988 | Igaue et al. ............ | 604/385.26 |
| 5,147,487 A | 9/1992 | Nomura et al. | |
| 5,330,598 A | 7/1994 | Erdman et al. | |
| 5,389,173 A | 2/1995 | Merkatoris et al. | |
| 5,415,649 A * | 5/1995 | Watanabe et al. ...... | 604/385.29 |
| 5,836,932 A | 11/1998 | Buell et al. | |
| 5,858,151 A | 1/1999 | Igaue et al. | |
| 5,879,500 A | 3/1999 | Herrin et al. | |
| 6,132,410 A * | 10/2000 | Van Gompel et al. .. | 604/385.25 |
| 6,217,563 B1 * | 4/2001 | Van Gompel et al. ...... | 604/385.101 |
| 6,312,420 B1 * | 11/2001 | Sasaki et al. .......... | 604/385.28 |

(Continued)

FOREIGN PATENT DOCUMENTS

EP 0048011 3/1982

(Continued)

OTHER PUBLICATIONS

"Concavity," Wikipedia, http://en.wikipedia.org/wiki/Concave, p. accessed Jul. 18, 2005.*

(Continued)

*Primary Examiner*—Tatyana Zalukaeva
*Assistant Examiner*—Keshia Gibson
(74) *Attorney, Agent, or Firm*—Lowe Hauptman & Berner, LLP (57) ABSTRACT

A disposable pants-type diaper includes a front waist region sheet, a rear waist region sheet and a body fluid absorbent pad. The front and rear waist region sheets are bonded together in the vicinity of transversely opposite side edges thereof and the pad is curved in a U-shape and has longitudinally opposite ends bonded to the inner side of the front and rear waist region sheets. Periphery of a lower edge of the front waist region sheet draws a curve which is convex upward and this-lower edge intersects transversely opposite side edges of the pad to define tops of a pair of leg-holes. A first elastic member extending along the lower edge of the front waist region sheet intersects third elastic members of the pad in the vicinity of the tops and then descend rearward of the diaper.

9 Claims, 9 Drawing Sheets

U.S. PATENT DOCUMENTS

| | | | |
|---|---|---|---|
| 6,514,233 B1 * | 2/2003 | Glaug | 604/385.25 |
| 6,554,815 B1 * | 4/2003 | Umebayashi | 604/385.27 |
| 6,582,414 B1 * | 6/2003 | Richardson | 604/385.24 |
| 2005/0010188 A1 * | 1/2005 | Glaug et al. | 604/396 |

FOREIGN PATENT DOCUMENTS

| | | |
|---|---|---|
| EP | 0 688 551 | 12/1995 |
| EP | 0 797 970 | 10/1997 |
| EP | 0 832 628 | 4/1998 |
| EP | 1 240 881 | 9/2002 |
| JP | 62-243806 | 10/1987 |
| JP | 1991-139349 A | 6/1991 |
| JP | 03-176053 | 7/1991 |
| JP | 9-224973 | 9/1997 |

OTHER PUBLICATIONS

Illustration A. Examiner's Diagram of Concavity and Convexity in relation to direction.*

* cited by examiner

DISPOSABLE PANTS-TYPE DIAPER HAVING FRONT PANEL WITH ELASTICIZED LOWER EDGE

BACKGROUND OF THE INVENTION

This invention relates to a disposable pants-type diaper for absorption and containment of body wastes.

Japanese Patent Application No. 1987-243806A discloses a disposable pants-type diaper composed of a front waist region, a rear waist region and a crotch region extending between these two waist regions. As viewed in its flatly developed state, semi-elliptic cutouts destined to define respective leg-holes are shaped so as to be put aside toward the front waist region with respect to a center line X bisecting a longitudinal length of the diaper. The diaper developed in this manner is folded back along the center line X to be placed one half upon another half and transversely opposite side edges are put flat and bonded together to obtain the pants-type diaper. In the pants-type diaper obtained in this manner, tops of the respective leg-holes lie in the front waist region. In this diaper, elastic members horizontally extending in a transverse direction of the diaper cooperate with elastic members vertically extending in a longitudinal direction of the diaper to surround the respective leg-holes. The tops of the respective leg-holes come substantially in coincidence with thigh tops of a baby wearing this diaper as the baby sits on the floor, so there is no anxiety that the tops of the respective leg-holes might uncomfortably compress the thigh tops of the baby.

Japanese Patent Application No. 1991-139349A also discloses a disposable pants-type diaper composed of a front waist region, a rear waist region and a crotch region extending between these two waist regions. In this diaper, elastic members provided in the front waist region so as to extend downward from a top of the front waist region drawing a circular arc, elastic members provided in the rear waist region so as to extend downward from a top of the rear waist region drawing a circular arc and elastic members provided in the crotch region so as to extend in back-and-forth direction cooperate together to surround respective thighs of the wearer.

Also in the case of the diaper disclosed in the above-cited Publication No. 1987-243806A, there is no serious anxiety that the tops of the respective leg-holes might uncomfortably compress the thigh tops of a baby wearing this diaper as the baby sits on the floor. However, the elastic members extend in no parallel to the leg-holes and may sometimes compress the tops of the respective thighs.

Figure 10:
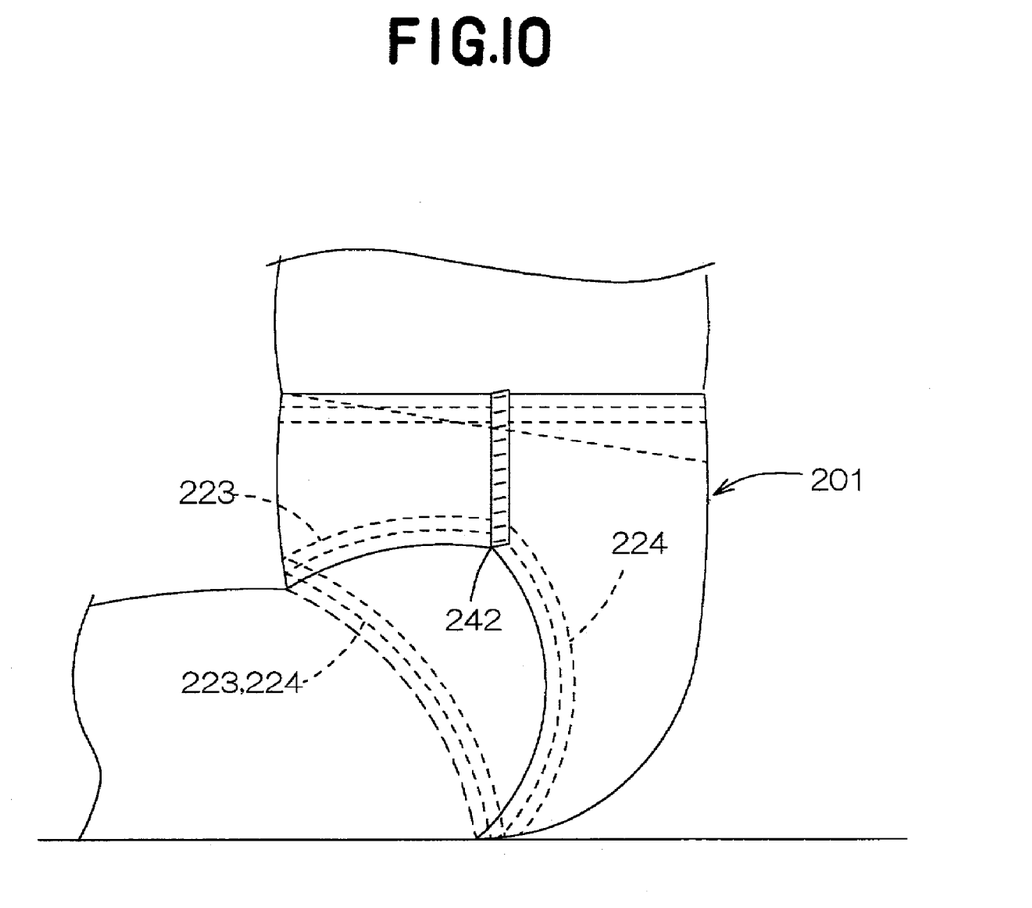
FIG. 10 is a side view illustrating the conventional pants-type diaper worn by a baby sitting on the floor.

FIG. 10 of the accompanying drawings is a fragmentary side view illustrating a baby wearing the diaper 201 disclosed in the Publication No. 1991-139349A and sitting on the floor. With this diaper 201, both the tops 242 of the leg-holes and the elastic members 223, 224 extending along these tops 242 lie on transversely opposite side edges of the diaper 201 not in coincidence with the tops of the thighs. In consequence, these elastic members 223, 224 may compress the tops of baby's thighs and slide down as indicated by imaginary lines.

SUMMARY OF THE INVENTION

It is an object of this invention to improve the diaper well known from the disclosures of above-cited Publication so that elastic members associated with leg-holes might neither compress tops of baby's thighs nor slide down as the baby sits on the floor.

According to this invention, there is provided a disposable pants-type diaper comprising a front waist region sheet contoured by a first upper edge extending in a horizontal direction or a transverse direction of the diaper, a pair of first side edges intersecting the first upper edge and extending in parallel to and spaced from each other and intersecting the first upper edge and a first lower edge opposed to the first upper edge delineating a curve convex upward in a longitudinal direction of the diaper, a rear waist region sheet contoured by a second upper edge and a pair of second side edges extending in parallel to the first upper edge and first side edges, respectively, and a second lower edge opposed to the second edge delineating a curve convex downward in the longitudinal direction and a body fluid absorbent pad having inner and outer surfaces, wherein the front waist region sheet is bonded to the rear waist region sheet in the vicinity of the first and second side edges, the body fluid absorbent pad extending with an inner surface inside upward with its opposite ends curved in a U-shape and with an inner surface inside has its outer surface bonded to respective inner surfaces of the front and rear waist region sheets, the first and second upper edges of the front and rear waist region sheets define a waist-hole, the first and second lower edges of the front and rear waist region sheets together with the side edges of the pad define a pair of leg-holes, and elastic members extending in parallel to peripheral edges of these waist-hole and leg-holes impart an elastically stretchable property to the respective peripheral edges of these holes.

The pair of leg-holes has further respective tops as viewed in the vertical direction or the longitudinal direction of the diaper, the tops being defined by the first lower edge of the front waist region sheet and the side edges of the pad. The elastic members extending in parallel to the respective peripheral edges of the leg-holes comprise a first elastic member attached to the front waist region sheet in parallel to its first lower edge, a second elastic member attached to the rear waist region sheet in parallel to its second lower edge and third elastic members attached to the pad in parallel to its side edges. The first elastic member attached to the front waist region descends rearward of the diaper from the tops to the vicinity of the first side edges; the second elastic member descends from the vicinity of the second side edges rearward of the diaper. The first and second elastic members are substantially contiguous to each other in the vicinity of intersections of the first and second side edges; and the third elastic member intersects the first elastic member in the vicinity of the tops, and intersects the second elastic member at a position lower than the second side edges.

DETAILED DESCRIPTION OF THE PREFERRED EMBODIMENTS

Details of a disposable pants-type diaper according to this invention will be more fully understood from the description given hereunder in reference to the accompanying drawings.

Figure 1:
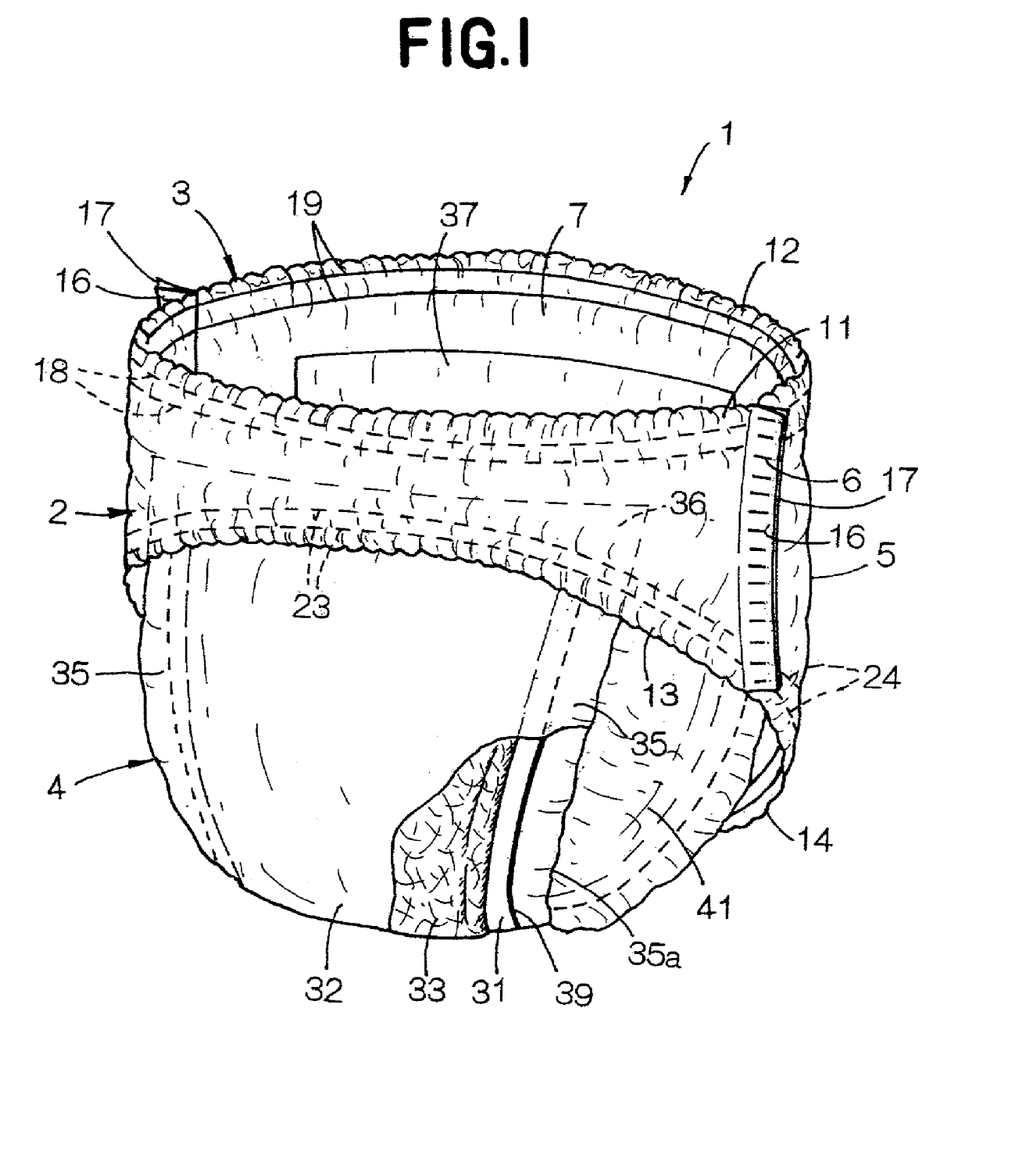
FIG. 1 is a partially cut away perspective view of the disposable pants-type diaper as viewed from the front side.
Figure 2:
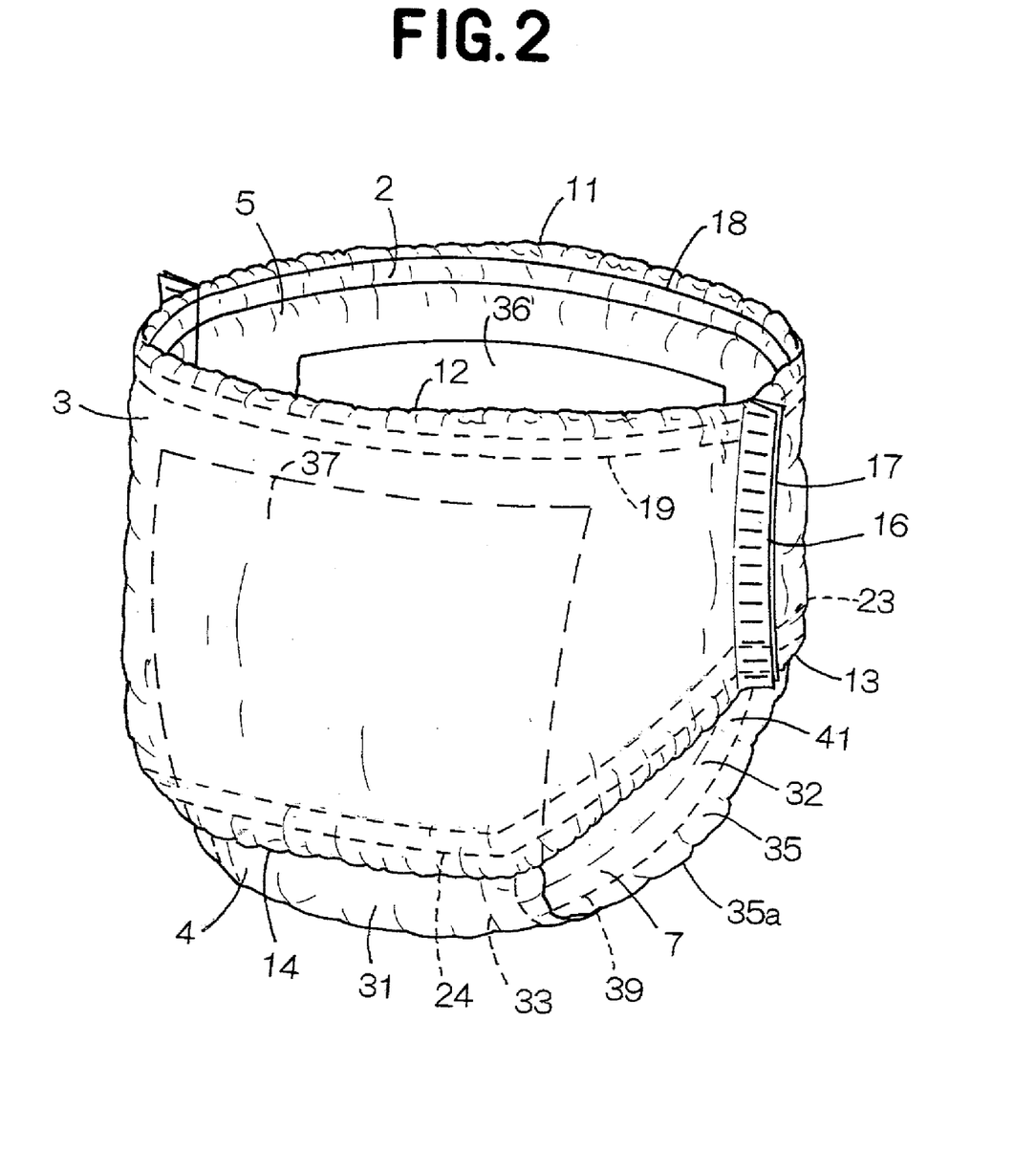
FIG. 2 is a perspective view of the diaper shown in FIG. 1 as viewed from the rear.

FIG. 1 is a partially cut away perspective view showing a disposable pants-type diaper 1 as viewed from its front side and FIG. 2 is a perspective view of the diaper 1 as viewed from its rear side. The diaper 1 comprises a front waist region sheet 2 lying on a front side of a wearer's waist, a rear waist region sheet 3 lying on a rear side of the wearer's waist and a body fluid absorbent pad 4 curved in a U-shape and lying in a crotch region. The front and rear waist region sheets 2, 3 are formed of a sheet material such as a nonwoven fabric, plastic film or laminated sheet consisting of these nonwoven fabric and film. A lateral width of each of these sheets 2, 3 is greater than half the circumferential dimension of the diaper 1 and transversely opposite side edges of these sheet 2,3 are overlaid and joined together at a plurality of zones 6 arranged intermittently in a longitudinal direction of the diaper 1 so as to form an annular waist region 5 and an annular waist-hole 7. The front and rear waist region sheets 2, 3 respectively have upper edges 11, 12 and lower edges 13, 14 extending in a transverse direction of the diaper 1, and pairs of side edges 16, 17 extending in parallel to each other in longitudinal direction of the diaper 1. These sheets 2, 3 are respectively provided on inner surfaces thereof with upper stretchable elastic members 18, 19, each comprising a plurality of elastic threads, extending in parallel to the upper edges 11, 12 and secured under extension thereto. These stretchable elastic members 18, 19 allow a peripheral edge of the waist-hole 7 to be placed against the wearer's waist with a uniform fitness. The front and rear waist region sheets 2, 3 are further provided on the inner surfaces thereof with lower stretchable elastic members 23, 24, each comprising a plurality of elastic threads, extending in parallel to the lower edges 13, 14 and secured under extension thereto.

The pad 4 comprises a liquid-pervious topsheet 31 facing the wearer's skin, a backsheet 32 facing the wearer's clothes and a body fluid absorbent core 33 interposed between these two sheets 31, 32. The top- and backsheets 31, 32 extend outward by beyond a peripheral edge of the core 33 and are overlaid and bonded together over respective extended zones so as to form a pair of flaps 35 outside the peripheral edge of the core 33. The pad 4 curved in a U-shape has front and rear upper ends 36, 37 of which the upper end 36 is bonded to an inner surface of the front waist region sheet 2 and the upper end 37 is joined to the inner surface of the rear waist region sheet 3. The flaps 35 are respectively provided along transversely opposite side edges 35a thereof with stretchable elastic members 39, each comprising a single elastic thread or a plurality of elastic threads, extending upwardly in a U-shape and bonded under extension to the inner surface of at least one of the top- and backsheets 31, 32. The side edges 35a of the respective flaps 35 corresponding to the side edges of the pad 4 intersect with the respective lower edges 13, 14 of the front and rear waist region sheets 2, 3 so as to form leg-holes 41. The stretchable elastic members 39 associated with the side edges of the pad 4 cooperate with the respective lower stretchable elastic members 23, 24 of the front and rear waist region sheets 2, 3 to form stretchable elastic members associated with the respective leg-holes of the diaper 1.

Figure 3:
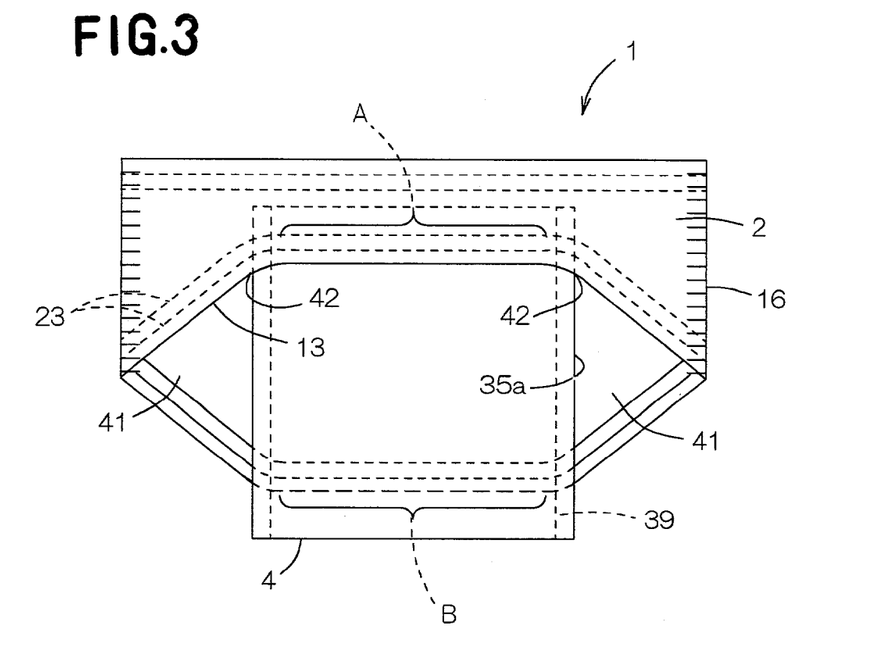
FIG. 3 is a front view of the diaper shown in FIG. 1.

FIG. 3 is a front view of the diaper 1. Periphery of the lower edge 13 of the front waist region sheet 2 draws a curved line which is convex upward. Intersections of this lower edge 13 with the respective side edges 35a of the pad 4 define respective tops 42 of the leg-holes 41 as viewed in a vertical direction. The lower stretchable elastic members 23 extend horizontally between the respective tops 42 of the leg-holes 41 and descend from the respective tops 42 rearward to the vicinity of the side edges 16. Such lower stretchable elastic members 23 intersect with the stretchable elastic members 39 extending along the side edges of the pad 4 in the vicinity of the respective tops 42.

Figure 4:
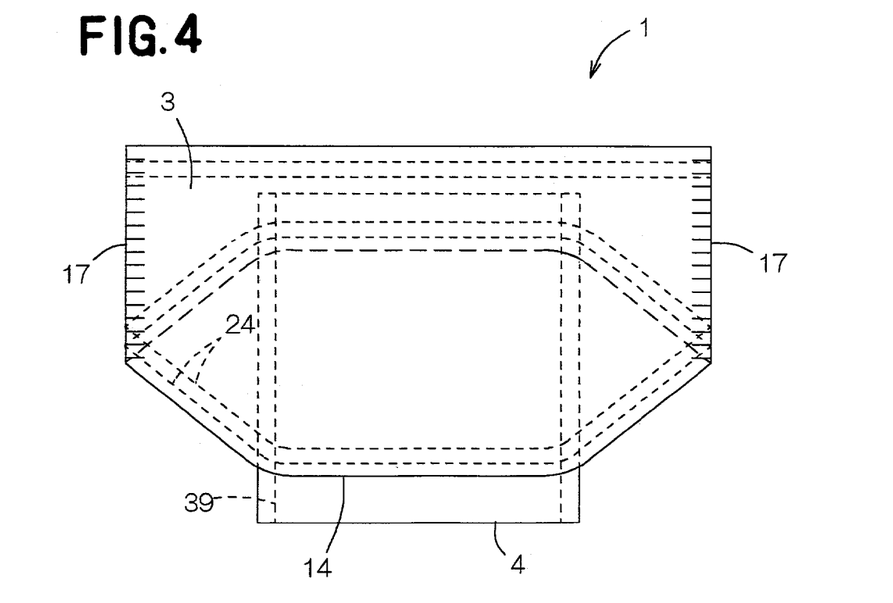
FIG. 4 is a rear view of the diaper shown in FIG. 1.

FIG. 4 is a rear view of the diaper 1. Periphery the lower edge 14 of the rear waist region sheet 3 draws a curved line which is convex downward. The lower elastic members 24 extend downward along the lower edge 14 of the rear waist region sheet 3 from the vicinity of the side edges 17 rearward and then extend horizontally across the pad 4. Such lower elastic members 24 intersect the elastic members 39 extending along the side edges of the pad 4 at a position lower than the side edges 17. Referring to FIGS. 3 and 4, the lower elastic members 23, 24 extending across the pad 4 function to bring the pad 4 in close contact with the wearer's body. If such function is not desired, it is possible to cut off the respective lower elastic members 23, 24 in the ranges A,B defined between the intersections of the lower elastic members 23, 24 with the elastic members 39 extending along the side edges of the pad 4.

Figure 5:
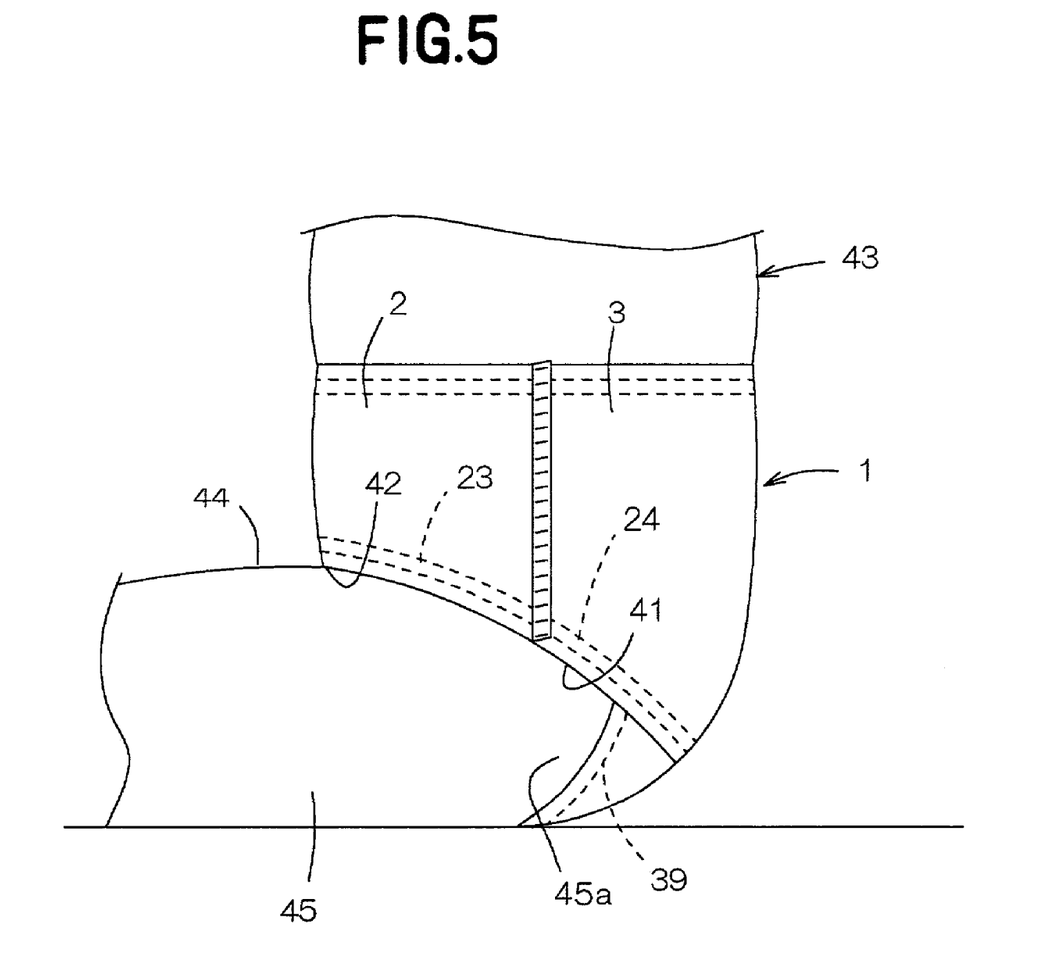
FIG. 5 is a side view illustrating the diaper worn by a baby sitting on the floor.

FIG. 5 is a fragmentary side view illustrating a baby 43 wearing the diaper 1 and sitting on the floor. As seen in FIG. 5, the tops 42 of the leg-holes 41 substantially coincide with respective tops 44 of the thighs 45b of the baby 43 and the lower elastic members 23, 24 of the front and rear waist region sheets 2, 3 are substantially contiguous to each other in the vicinity of the zones 6 in which the first side edges 16 and the second side edges 17 are bonded together. Consequently, the lower elastic members 23, 24 descend rearward from the tops 42 to a hip 45a of the baby 43, drawing substantially straight lines or gently curved lines. With the diaper 1 worn in this manner, stretch and contraction of the lower elastic members 23, 24 due to a movement of the thighs 45 and the hip 45a of the baby 43 occurring as the baby 43 sits on the floor as illustrated merely intensifies or weakens a tightening effect around the thighs 45 rather than causing the diaper 1 to slide down along the thighs 45 as has been the case with the diaper of well known art. In this way, position of the diaper 1 is stabilized around the thighs 45.

Figure 6:
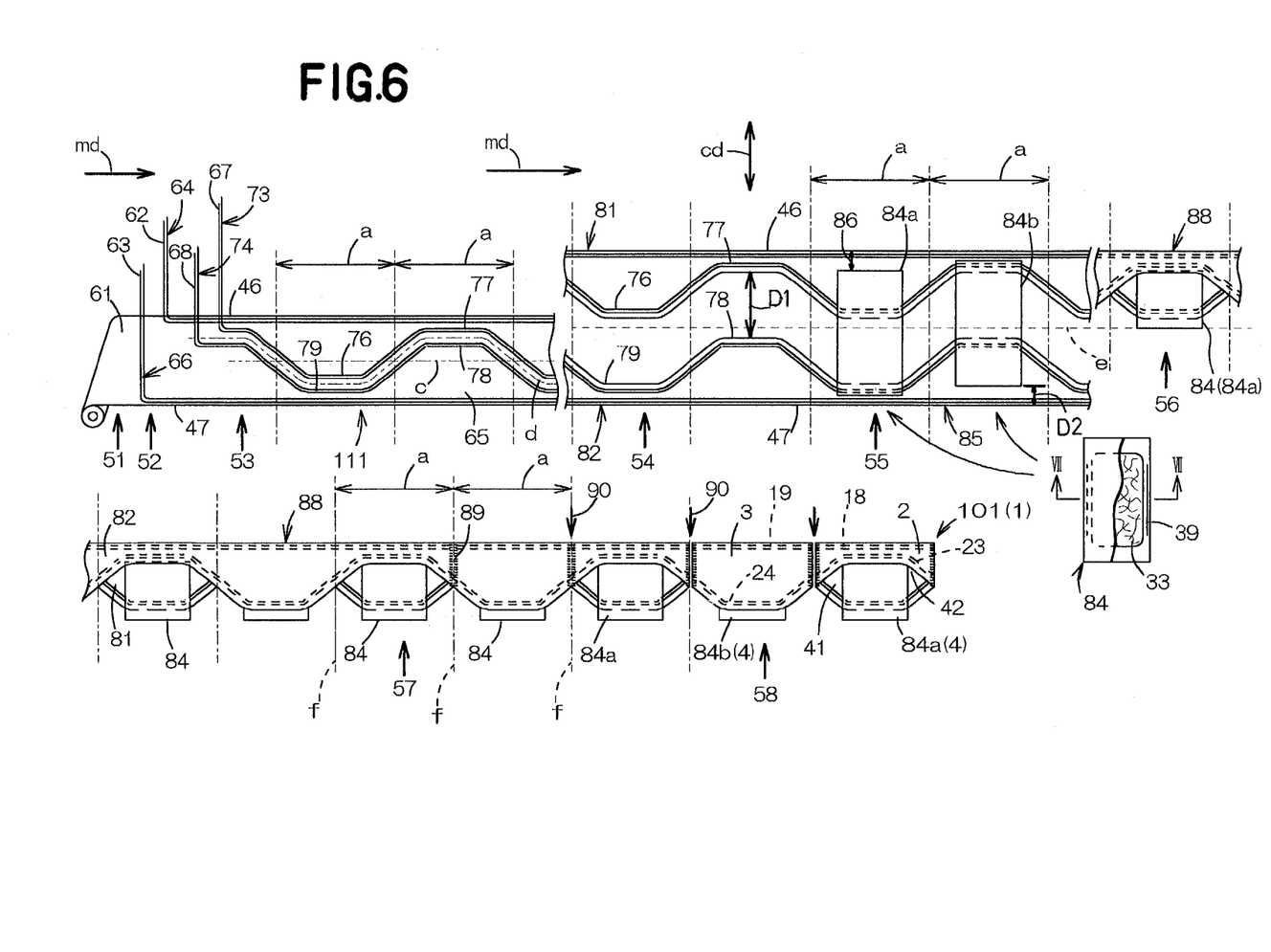
FIG. 6 is a diagram schematically illustrating a process for making the diaper shown in FIG. 1.

FIG. 6 is a diagram schematically illustrating important part of a process for making the diaper 1, in which a machine direction is indicated by an arrow md and a direction orthogonal to the machine direction is indicated by an arrow cd. The process comprises first—eight steps 51–58. In the first step 51, a single web 61 is continuously fed from the left side of the drawing in FIG. 6 to the machine direction md.

In the second step 52, the elastic members 64, 66 associated with the waist-hole, each comprising a plurality of elastic threads 62, 63, are continuously fed onto the respective side edges of the web 61 and attached to an upper surface of the web 61 by means of an adhesive (not shown). The adhesive may be applied to the elastic threads 62, 63 or on the web 61.

In the third step 53, a first elastic member 73 associated with one leg-hole comprising a plurality of elastic threads 67, and a second elastic member 74 associated with the other leg-hole comprising a plurality of elastic threads 68, are continuously fed under a desired extension onto the upper surface of the web 61 so as to draw substantially sinusoidal curves and attached thereto by means of an adhesive (not shown). In this way, a composite web 65 comprising the web 61 and the respective elastic members 64, 66, 73, 74 are obtained. The first elastic member 73 associated with the one leg-hole and the second elastic member 74 associated with the other leg-hole are symmetric about a center line c of the web 61 and shifted to the md direction by a length corresponding to half cycle a. More specifically, if the first elastic member 73 associated with one leg-hole is shifted in the machine direction md by the half cycle a from the state illustrated in FIG. 6, profile of a curve defined by a trough 76 and a crest 77 drawn by the first elastic member 73 associated with the one leg-hole will be symmetric to the corresponding profile of the curve defined by a crest 78 and a trough 79 drawn by the second elastic member 74 associated with the other leg-hole about the center line c.

In the fourth step 54, the web 61 is cut into a first half web 81 and a second half web 82 along a line d bisecting a width of the distance between the first elastic member 73 associated with the one leg-hole and the second elastic member 74 associated with the other leg-hole, and these two half webs 81, 82 are displaced in parallel to the direction cd orthogonal to the machine direction md to space these two half webs 81, 82 from each other by a desired dimension D1.

In the fifth step 55, individual body fluid absorbent pads 84, each of which is illustrated as partially cut away, are placed upon the first and second half webs 81, 82 so that the pads 84 may overlap these half webs 81, 82 and thereby connect them to each other. In the overlapping zones, the pads 84 are bonded to the respective half webs 81, 82 by means of an adhesive (not shown) to obtain a first continuum 85 of diapers. A dimension of the pad 84 in the machine direction md is shorter than the length corresponding to the half cycle a and one pad 84a of two pads 84 which are adjacent to each other in the machine direction md lies so as to be in the center of the trough 76 drawn by the first elastic member 73 associated with the one leg-hole and the trough 79 drawn by the second elastic member 74 associated with the other leg-hole. The other pad 84b lies so as to be in the center of the crest 77 drawn by the first elastic member 73 associated with the one leg-hole and the crest 78 drawn by the second elastic member 74 associated with the other leg-hole. In these adjacent pads 84a, 84b, a distance 86 from the one web side edge 46 to the pad 84a is equal to a distance D2 from the other web side edge 47 to the pad 84b. While the pads 84 really have the body fluid absorbent cores 33 and the elastic members 39 extending along the respective side edges thereof (See FIG. 7), FIG. 6 illustrates only an external shape of these pads 82 placed on the web 61. The first and second half webs 81, 82 and the first and second elastic members 73, 74 associated with the respective leg-holes underlying the pads 84 are indicated by imaginary lines to clarify the presence of these half webs 81, 82 and the elastic members 73, 74.

In the sixth step 56, the first continuum 85 of diapers is folded back onto itself along a center line e extending in the machine direction md and bisecting a dimension of this continuum 85 in the direction orthogonal to the machine direction md with the pads 84 inside to a second continuum 88 of diapers.

In the seventh step 57, the first and second half webs 81, 82 placed upon each other to form the second continuum 88 of diapers are bonded together in zones 89 extending along lines f each bisecting a distance between each pair of the adjacent pads 84, 84.

In the eighth step 58, the second continuum 88 of diapers is cut along lines indicated by arrows 90, i.e., along the lines f so as to bisect the respective zones 89 to right and left halves and thereby individual diapers 101 are obtained. As will be apparent from the diagram, each diapers 101 are obtained for every half cycle a of the substantially sinusoidal curves drawn by the first and second elastic members 73, 74 associated with the respective leg-holes. The diapers 101 having the pads 84a and showing their frontsides and the diapers 101 having the pads 84b and showing their rearsides are alternately obtained as the second continuum 88 of diapers is cut along the lines f. Whether the diapers 101 show frontsides or rearsides in the final step of the process for making the diaper, these individual diapers 101 are identical one to another. Specifically, these individual diapers 101 are identical one to another in that the elastic members 64, 66 associated with the waist-hole are placed upon each other and the first and second elastic members 73, 74 associated with the respective leg-holes are placed upon each other in the bonding zones 89.

Each of the diapers 101 obtained by the process described above corresponds to the diaper 1 shown in FIG. 1 and each of the pads 84 of the diapers 101 corresponds to the pad 4 of the diaper 1. In the case of the diapers 101 having the pad 84a, the first and second half webs 81, 82 respectively define the rear waist region sheet 3 and the front waist region sheet 2 of the diaper 1. The elastic members 64, 66 associated with the waist-hole respectively define the upper elastic members 19, 18 of the rear waist region sheet 3 and the front waist region sheet 2 in the diaper 1. The first and second elastic members 73, 74 respectively define the lower elastic members 24, 23 of the front waist region sheet 2 and the rear waist region sheet 3 in the diaper 1. In the case of the diapers 101 having the pad 84b, the first and second half webs 81, 82 respectively define the front waist region sheet 2 and the rear waist region sheet 3 of the diaper 1. The elastic members 64, 66 associated with the waist-hole respectively define the upper elastic members 18, 19 of the rear waist region sheet 3 and the front waist region sheet 2 in the diaper 1. The first and second elastic members 73, 74 respectively define the lower elastic members 23, 24 of the front waist region sheet 2 and the rear waist region sheet 3 in the diaper 1. In the case of the diapers 101 having the pad 84a, the respective tops 42 of the leg-holes 41 in the diaper 1 are defined by the intersections of the second half web 82 and the pad 84a. In the case of the diaper 101 having the pad 84b, on the other hand, the respective tops 42 of the leg-holes 41 in the diaper 1 are defined by the intersections (not shown) of the first half web 81 and the pad 84b.

A stock material for the web 61 used in this process may be selected from a group of materials including a nonwoven fabric, a plastic film and a composite sheet consisting of these nonwoven fabric and plastic film. The web 61 may be liquid-impervious or breathable and liquid-impervious or liquid-pervious. The first and second elastic members 73, 74 drawing substantially sinusoidal curves have the respective crests 77, 78 and the troughs 76, 79 which may be rectilinear in parallel to the center line c of the web 61 as illustrated or curvilinear. The number of the elastic threads 67, 68 respectively forming the first and second elastic members 73, 74 associated with the leg-holes may be appropriately increased or reduced.

Figure 7:
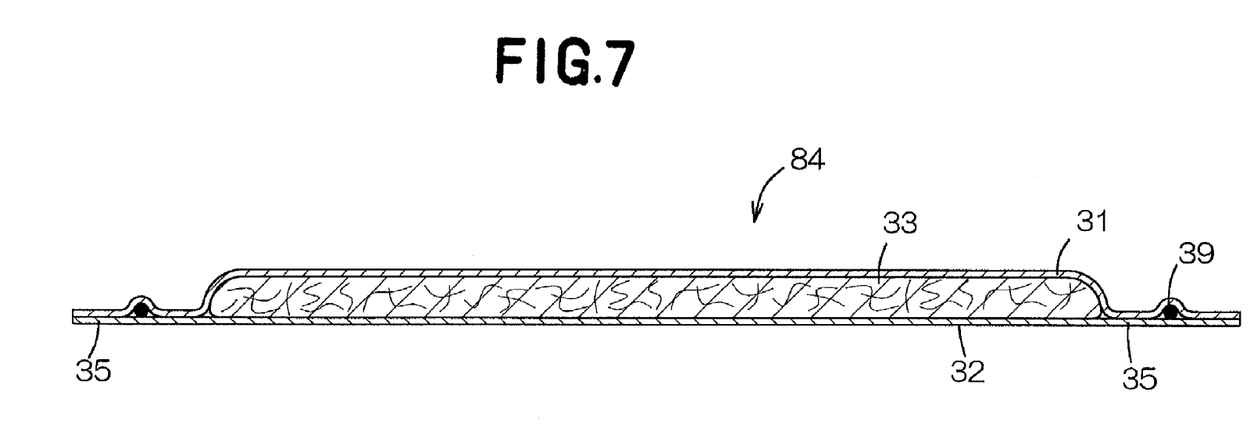
FIG. 7 is a cross-sectional view of the pad shown in FIG. 6 as taken along a line VII—VII in FIG. 6.

FIG. 7 is a cross-sectional view of the pad 84 as taken along a line VII–VII in FIG. 6. The pad 84 is the same as the pad 4 shown in FIG. 1, i.e., comprises the liquid-pervious topsheet 31, the liquid-impervious backsheet 32 and the body fluid absorbent core 33 interposed between these two sheets 31, 32. In the flaps 35 extending outside the side edges of the core 33, the elastic members 39 extend along the side edges of these flaps 35 and disposed between the top and backsheets 31, 32. The topsheet 31 may be formed of a nonwoven fabric or an apertured plastic film and the backsheet 32 may be formed of a plastic film.

Figure 8:
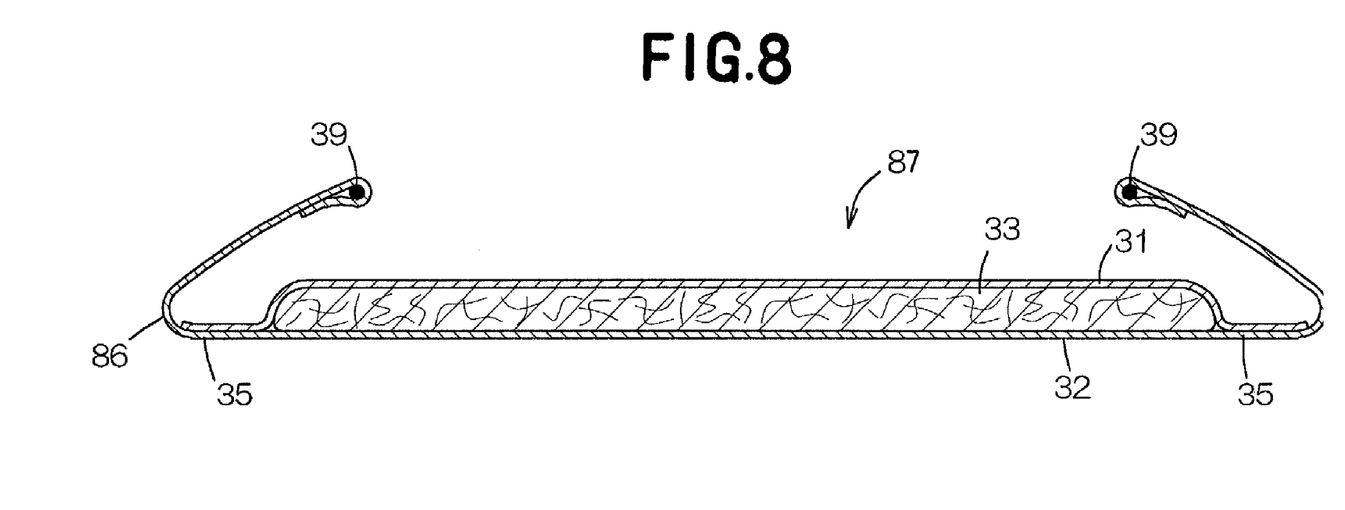
FIG. 8 is a cross-sectional view similar to FIG. 7 but showing another embodiment of the pad.

FIG. 8 is a view similar to FIG. 7 but showing a pad 87 according to another embodiment replacing the pad 84 shown in FIG. 7. In the case of this pad 87, portion of the backsheet 32 extending outwardly beyond the topsheet 31 in the flaps 35 is folded back onto inner side of the pad 87. The elastic members 39 extending along the side edges of the flaps 35 lie slightly inside above the pad 35. In the case of this pad 87, folded regions 87 of the respective flaps 35 partially form the respective leg-holes. While external shapes of all the illustrated pads 4, 84, 87 are rectangular, shapes of these pads may be hourglass-shaped, in which the side edges 35a are curved inward in middle zones to rear and front directions thereof. In this case, the elastic members 39 may extend in the rear and front directions along the curved side edges 35a.

Figure 9:
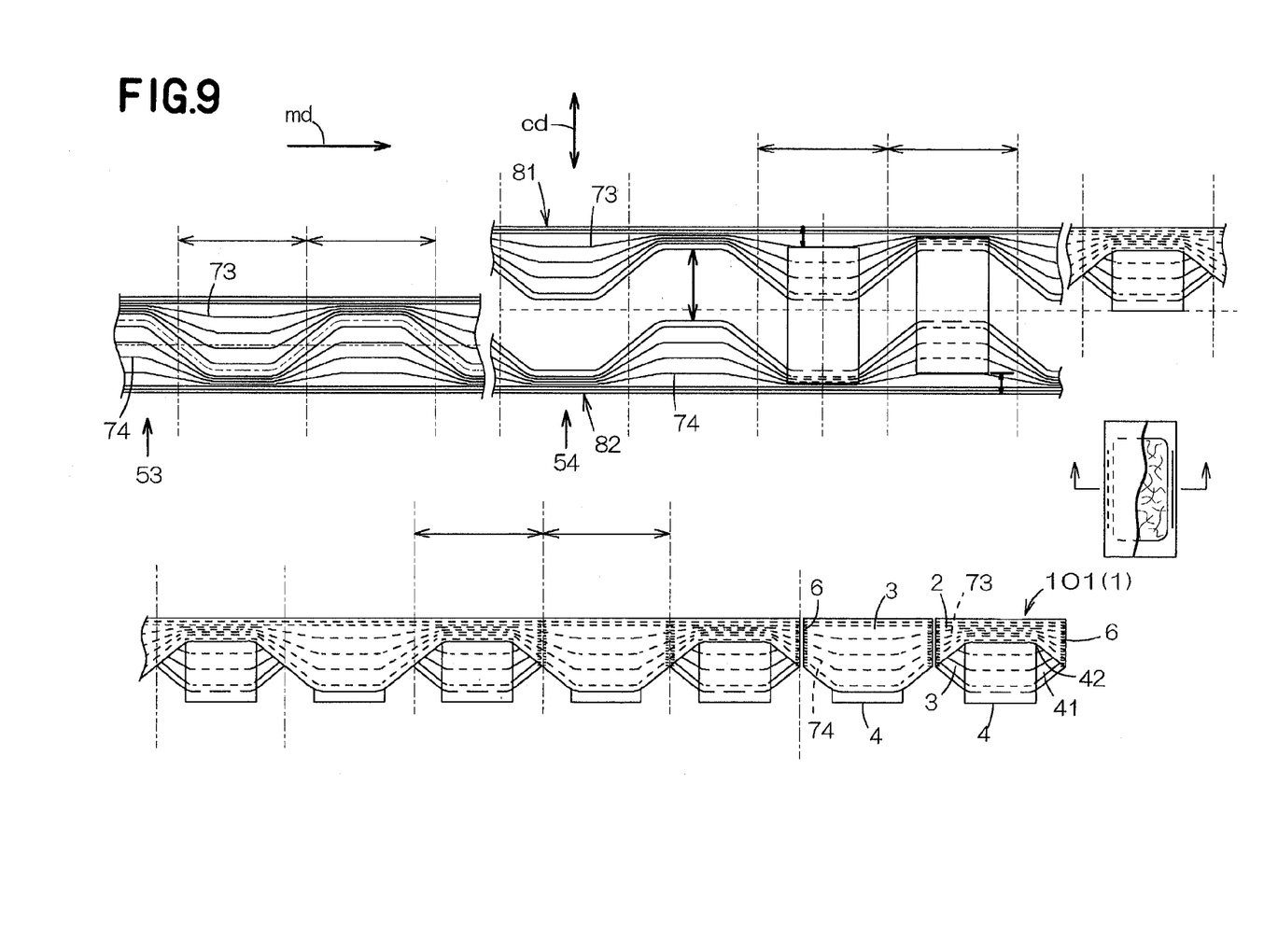
FIG. 9 is a diagram similar to FIG. 6 but illustrating another embodiment of the process for making the diaper.

FIG. 9 is a view similar to FIG. 6 but illustrating a part of the process of another embodiment for making the diapers 101. In the third step 53 of this alternative process, the first and second elastic members 73, 74 each comprising a plurality of elastic threads under extension are fed onto the regions of the web corresponding to the first and second half webs 81, 82 in the fourth step 54 so that these elastic members 73, 74 may be distributed uniformly as much as possible over the direction cd. While the respective components of the diapers 101 obtained in this manner are designated by reference numerals similar to those in the diaper 1 shown in FIG. 1, both the front waist region sheet 2 and the rear waist region sheet 3 are stretchable and contractible in the transverse direction of the diaper 1. On the front waist region sheet 2, the elastic member 73 or 74 associated with the leg-hole lying in the vicinity of each of the leg-holes 41 descends from the top 42 of each of the leg-holes 41 toward the bonding zones 6 and, on the rear waist region sheet 3, the elastic member 73, 74 lying in the vicinity of the leg-hole 41 extends along the leg-hole 41 and descends from the bonding zones 6 toward the pad 4. In such diapers 101 also, the elastic member 73 or 74 extending along the peripheral edge one of the leg-holes 41 extends rearward from the top 42 drawing a substantially straight line, so there is no anxiety that the elastic members 73, 74 associated with the leg-holes 41 might slide down along the thighs 45 even if the baby wearing the diapers 101 sits on the floor as illustrated in FIG. 5.

While the front and rear waist region sheets 2, 3 of the diaper 1, 101 are respectively formed by a single layered sheet material in the embodiments as illustrated and described, these sheets 2, 3 may be respectively formed by a laminated sheet material each comprising two layers of a sheet material. In such case, the upper elastic members 18, 19 and the lower elastic members 23, 24 are preferably interposed between these two layers of sheet material and bonded to the inner surface of one of these two layers of a sheet material. In the diaper 1 shown in FIGS. 1 and 2, not only the longitudinally opposite ends 36, 37 of the pad 4 but also the zones of the pad 4 in which the elastic members 39 intersect the lower elastic members 23, 24 may be bonded to the front and rear waist region sheets 2, 3 to improve fitness of the diaper 1 to the wearer around the wearer's thighs.

The disposable pants-type diaper according to this invention is characterized in that the tops of the leg-holes lie in the front waist region and the elastic members associated with the leg-holes descend from the respective tops thereof rearward drawing substantially straight lines. Such unique arrangement is effective to avoid the anxiety that the elastic members associated with the leg-holes might slide down along the thighs even if the baby wearing this diaper sits on the floor.

What is claimed is:

1. A disposable pants-type diaper, comprising:
   a front waist panel contoured by a first upper edge, a pair of first side edges extending downwardly from said first upper edge and being spaced from each other, and a first lower edge being opposed to said first upper edge and convex upward towards said first upper edge;
   a rear waist panel contoured by a second upper edge, a pair of second side edges extending downwardly from said second upper edge and being spaced from each other, and a second lower edge being opposed to said second upper edge and convex downward away from said second upper edge;
   a pad comprising a topsheet, backsheet, and a body fluid absorbent core disposed between said topsheet and said backsheet defining a crotch region of said diaper and having opposite ends bonded to said front and rear waist panels, respectively;
   said front waist panel being bonded to said rear waist panel along said first and second side edges, and said first and second upper edges defining a waist opening;
   said first and second lower edges of said front and rear waist panels together with side edges of said absorbent pad defining a pair of leg openings, wherein the highest point of each of said leg openings is located where said first lower edge of said front waist panel crosses over the respective side edge of said absorbent pad.

2. The diaper according to claim 1, further comprising
   a first elastic member attached to said front waist panel along the first lower edge; and
   a second elastic member attached to said rear waist panel along the second lower edge;
   wherein at least one of said first and second elastic members is discontinuous between places where the respective first and second lower edges cross over said side edges of said pad.

3. The diaper according to claim 1, wherein said first and second lower edges are imaginary extensions of each other in the vicinity of said first and second side edges where the front and rear waist panels are bonded to each other.

4. The diaper according to claim 1, wherein, in the vicinity of said first and second side edges where the front and rear waist panels are bonded to each other, said first and second lower edges are substantially straight and extend continuously from the highest points of said leg openings rearwardly downwardly.

5. The diaper according to claim 1, wherein the side edges of said pad cross over said second lower edge at places located below lowest points of said second side edges.

6. The diaper according to claim 1, wherein said front waist panel, said rear waist panel and said pad are separate pieces bonded to together.

7. The diaper according to claim 1, wherein the crotch region is defined solely by said pad.

8. The diaper according to claim 1, wherein said front and rear waist panels have complementary shapes.

9. The diaper according to claim 8, wherein said complementary shapes of said front and rear waist panels are defined by said upwardly convex first lower edge and said downwardly convex second lower edge.

* * * * *